United States Patent [19]

Quadranti et al.

[11] Patent Number: 5,407,898
[45] Date of Patent: Apr. 18, 1995

[54] SYNERGISTIC COMPOSITION AND METHOD FOR THE SELECTIVE CONTROL OF WEEDS

[75] Inventors: Marco Quadranti, Brugg; Willy Maurer, Riehen, both of Switzerland

[73] Assignee: Ciba-Geigy Corporation, Ardsley, N.Y.

[21] Appl. No.: 206,103

[22] Filed: Mar. 2, 1994

Related U.S. Application Data

[63] Continuation of Ser. No. 901,489, Jun. 19, 1992, abandoned, which is a continuation of Ser. No. 272,849, Nov. 18, 1988, abandoned.

[30] Foreign Application Priority Data

Nov. 27, 1987 [CH] Switzerland ............... 4629/87-1

[51] Int. Cl.$^6$ ................. A01N 43/54; A01N 37/22
[52] U.S. Cl. ................. 504/136; 504/105; 504/149; 504/243; 504/341; 504/342
[58] Field of Search ............... 504/136, 149, 243, 342, 504/105, 341

[56] References Cited

U.S. PATENT DOCUMENTS

| | | | |
|---|---|---|---|
| H670 | 9/1989 | Kimura et al. | 504/132 |
| 3,547,620 | 12/1970 | Olin | 504/342 |
| 3,937,730 | 2/1976 | Vogel et al. | 504/342 |
| 4,478,635 | 10/1984 | Meyer et al. | 544/321 |
| 5,201,933 | 4/1993 | Miller et al. | 504/104 |
| 5,206,021 | 4/1993 | Dookhith et al. | 514/938 |
| 5,215,570 | 6/1993 | Burckhardt et al. | 504/104 |
| 5,256,630 | 10/1993 | Bussler | 504/134 |

FOREIGN PATENT DOCUMENTS 0236273 9/1987 European Pat. Off. .

OTHER PUBLICATIONS

The Agrochemicals Handbook, 2nd Edition, Aug. 1987, The Royal Society of Chemistry, Nottingham (England), pp. A004 and A278.

*Primary Examiner*—Allen J. Robinson
*Assistant Examiner*—John D. Pak
*Attorney, Agent, or Firm*—Kevin T. Mansfield

[57] ABSTRACT

The invention relates to a herbicidal composition containing as compound of formula I N-[2-(methoxycarbonyl)phenyl]sulfonyl-N'-(4,6-bis-difluoromethoxypyrimidin-2-yl)-urea together with a herbicide of formula III

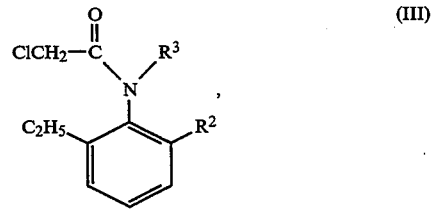

wherein the radicals $R^2$ and $R^3$ are as defined in the text, to a method for the selective control of weeds in crops of useful plants and to the use of these compositions for controlling weeds in crops of useful plants.

5 Claims, No Drawings

SYNERGISTIC COMPOSITION AND METHOD FOR THE SELECTIVE CONTROL OF WEEDS

This is a continuation of Ser. No. 901,489, filed on Jun. 19, 1992, now abandoned, which is a continuation of Ser. No. 272,849, filed on Nov. 18, 1988, now abandoned.

The present invention relates to a synergistic composition containing a herbicidal combination of active ingredients. The composition according to the invention is suitable for the selective control of weeds in crops of useful plants, especially in maize.

The invention relates also to a method of controlling weeds in crops of useful plants, preferably in maize, and to the use of this novel composition.

EP-A 0084020 discloses N-[2-(methoxycarbonyl)-phenyl]sulfonyl-N'-(4,6-bis-difluoromethoxypyrimidin-2-yl)-urea of formula I

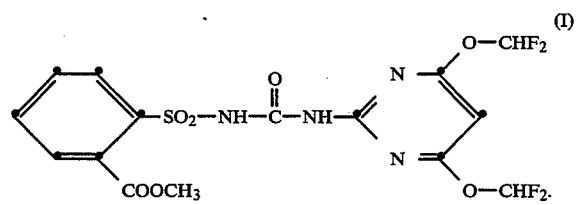

This compound has good selective herbicidal action against weeds in crops of useful plants.

In addition, the compounds of formulae II to VIII are known as herbicidal active ingredients some of which exhibit good selectivity in crops of useful plants. Some of the compounds of formulae II to VIII are commercially available.

There may be mentioned as compounds of formulae II to VIII:

a) 2-Chloro-4-ethylamino-1,3,5-triazines of formula II

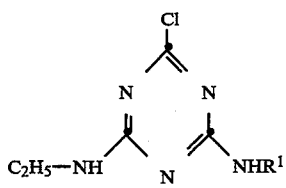

wherein
$R^1$ is isopropyl, tert.-butyl or 1-cyano-1-methylethyl.
Formula II includes the following individual compounds:
IIa) 2-chloro-4-ethylamino-6-isopropylamino-1,3,5-triazine, common name "atrazine" (described in "The Pesticide Manual", 8th ed. (1987), p. 36, Ed. C. R. Worthing; The British Crop Protection Council, Thornton Heath, GB)
IIb) 2-chloro-4-ethylamino-6-(1-cyano-1-methylethylamino)-1,3,5-triazine; common name "cyanazine" (described in "The Pesticide Manual", 8th ed. (1987), p. 198, Ed. C. R. Worthing; The British Crop Protection Council, Thornton Heath, GB)
IIc) 2-chloro-4-ethylamino-6-tert.-butylamino-1,3,5-triazine; common name "terbuthylazine"; (described in "The Pesticide Manual", 8th ed. (1987), p. 778, Ed. C. R. Worthing; The British Crop Protection Council, Thornton Heath, GB).

b) Chloroacetanilides of formula III

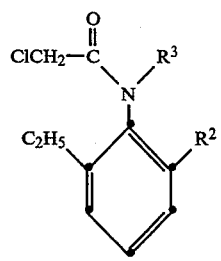

wherein
$R^2$ is methyl or ethyl and
$R^3$ is methoxymethyl or 2-methoxy-1-methylethyl.
Formula III includes, especially, the following individual compounds:
IIIa) 2-chloro-2'-ethyl-6'-methyl-N-(2-methoxy-1-methylethyl)-acetanilide; common name "metolachlor"; (described in "The Pesticide Manual", 8th ed. (1987), p. 568, Ed. C. R. Worthing; The British Crop Protection Council, Thornton Heath, GB) and
IIIb) 2-chloro-2',6'-diethyl-N-methoxymethyl-acetanilide; common name "alachlor"; (described in "The Pesticide Manual", 8th ed. (1987), p. 5, Ed. C. R. Worthing; The British Crop Protection Council, Thornton Heath, GB).

c) Phenols of formula IV

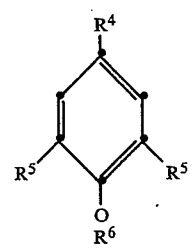

wherein
$R^5$ is bromine or iodine and
$R^4$ is CN or the radical

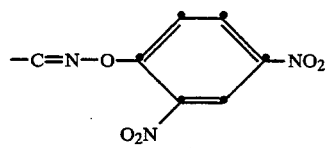

when
$R^6$ is hydrogen, or
$R^4$ is CN when
$R^6$ is $CO-(CH_2)_6-CH_3$.

Formula IV includes, especially, the following individual compounds:
IVa) 4-hydroxy-3,5-diiodobenzonitrile; common name "ioxynil"; (described in "The Pesticide Manual", 8th ed. (1987), p. 479, Ed. C. R. Worthing; The British Crop Protection Council, Thornton Heath, GB)
IVb) 4-hydroxy-3,5-dibromobenzonitrile; common name "bromoxynil"; (described in "The Pesticide Manual", 8th ed. (1987), p. 100, Ed. C. R. Worthing; The British Crop Protection Council, Thornton Heath, GB)

IVc) 3,5-dibromo-4-hydroxybenzaldehyde 2,4-dinitrophenyloxime; common name "bromofenoxim"; (described in "The Pesticide Manual", 8th ed. (1987), p. 94, Ed. C. R. Worthing; The British Crop Protection Council, Thornton Heath, GB)

IVd) octanecarboxylic acid 2,6-dibromo-4-cyanophenol ester; common name "bromoxynil octanoate"; (described in "The Pesticide Manual", 8th ed. (1987), p. 100, Ed. C. R. Worthing; The British Crop Protection Council, Thornton Heath, GB).

d) Dichloroarylcarboxylic acids of formula V

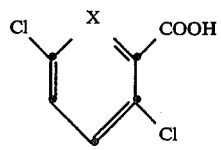

wherein
X is

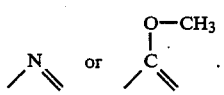

Formula V includes the following individual compounds:

Va) 3,6-dichloropicolinic acid; common name "clopyralid"; (described in "The Pesticide Manual", 8th ed. (1987), p. 189, Ed. C. R. Worthing; The British Crop Protection Council, Thornton Heath, GB)

Vb) 3,6-dichloro-2-methoxybenzoic acid; common name "dicamba"; (described in "The Pesticide Manual", 8th ed. (1987), p. 251, Ed. C. R. Worthing; The British Crop Protection Council, Thornton Heath, GB).

e) As a compound of formula VI

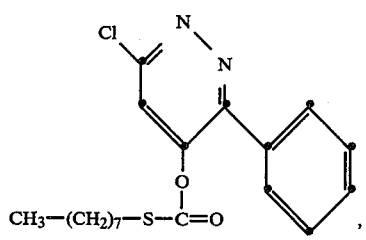

6-chloro-3-phenylpyridazin-4-yl S-octyl thiocarbonate; common name "pyridate"; (described in "The Pesticide Manual", 8th ed. (1987), p. 731, Ed. C. R. Worthing; The British Crop Protection Council, Thornton Heath, GB).

f) As a compound of formula VII

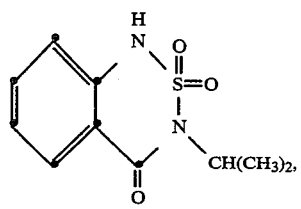

3-isopropyl-1H-2,1,3-benzothiadiazin-4(3H)-one 2,2-dioxide; common name "bentalone"; (described in "The Pesticide Manual", 8th ed. (1987), p. 63, Ed. C. R. Worthing; The British Crop Protection Council, Thornton Heath, GB).

g) 4-chlorophenoxyacetic acid derivatives of formula VIII

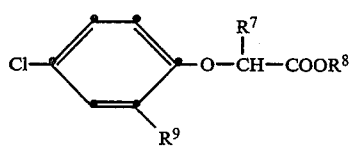

wherein
$R^7$ is hydrogen; or methyl;
$R^8$ is hydrogen; $C_1$-$C_8$alkyl; $C_1$-$C_4$alkoxy-$C_1$-$C_2$alkyl; or a cation equivalent of an alkali metal or an alkaline earth metal, or of an ammonium, di-($C_1$-$C_4$)alkylammonium, di-hydroxyethylammonium or trihydroxyethylammonium ion; and
$R^9$ is chlorine; or methyl.

Formula VIII includes, especially, the following individual compounds:

VIIIa) 2,4-dichlorophenoxyacetic acid; common name "2,4-D"; (described in "The Pesticide Manual", 8th ed. (1987), p. 220, Ed. C. R. Worthing; The British Crop Protection Council, Thornton Heath, GB).

VIIIb) 2,4-dichlorophenoxyacetic acid 2-butoxyethyl ester; common name "2,4-D-(2-butoxyethyl)"; (described in "The Pesticide Manual", 8th ed. (1987), p. 220, Ed. C. R. Worthing; The British Crop Protection Council, Thornton Heath, GB).

VIIIc) 2,4-dichlorophenoxyacetic acid isooctyl ester: common name "2,4-D-(iso-octyl)"; (described in "The Pesticide Manual", 8th ed. (1987), p. 220, Ed. C. R. Worthing; The British Crop Protection Council, Thornton Heath, GB).

VIIId) 2,4-dichlorophenoxyacetic acid butyl ester; common name "2,4-D(butyl)"; (described in "The Pesticide Manual", 8th ed. (1987), p. 220, Ed. C. R. Worthing; The British Crop Protection Council, Thornton Heath, GB).

VIIIe) 2,4-dichlorophenoxyacetic acid dimethylammonium salt; common name "2,4-D-dimethyl--ammonium"; (described in "The Pesticide Manual" 8th ed. (1987), p. 220, Ed. C. R. Worthing; The British Crop Protection Council, Thornton Heath, GB).

VIIIf) 2,4-dichlorophenoxyacetic acid bis-(2-hydroxyethyl)ammonium salt; common name "2,4-D-bis-(2-hydroxyethyl)ammonium"; (described in "The Pesticide Manual", 8th ed. (1987), p. 220, Ed. C. R. Worthing; The British Crop Protection Council, Thornton Heath, GB).

VIIIg) 2,4-dichlorophenoxyacetic acid tris-(2-hydroxyethyl)ammonium salt; common name "2,4-D-tris-(2-hydroxyethyl)ammonium" (described in "The Pesticide Manual", 8th ed. (1987), p. 220, Ed. C. R. Worthing; The British Crop Protection Council, Thornton Heath, GB).

VIIIh) 2-(4-chloro-2-methylphenoxy)-propionic acid; common name "mecoprop"; (described in "The Pesticide Manual", 8th ed. (1987), p. 522, Ed. C. R. Worthing; The British Crop Protection Council, Thornton Heath, GB).

VIIIi) 2-(4-chloro-2-methylphenoxy)-propionic acid potassium salt; common name "mecoprop-potassium"; (described in "The Pesticide Manual", 8th ed. (1987), p. 522, Ed. C. R. Worthing; The British Crop Protection Council, Thornton Heath, GB).

VIIIj) 2-(2,4-dichlorophenoxy)-propionic acid; common name "dichlorprop"; (described in "The Pesticide Manual", 8th ed. (1987), p. 267, Ed. C. R. Worthing; The British Crop Protection Council, Thornton Heath, GB).

VIIIk) 2-(2,4-dichlorophenoxy)-propionic acid potassium salt; common name "dichlorprop-potassium"; (described in "The Pesticide Manual", 8th ed. (1987), p. 267, Ed. C. R. Worthing; The British Crop Protection Council, Thornton Heath, GB).

VIIIl) 2-(2,4-dichlorophenoxy)-propionic acid ethylammonium salt; common name "dichlorprop-ethylammonium"; (described in "The Pesticide Manual", 8th ed. (1987), p. 267, Ed. C. R. Worthing; The British Crop Protection Council, Thornton Heath, GB).

VIIIm) 2-(2,4-dichlorophenoxy)-propionic acid isooctyl ester; common name "dichlorprop-isooctyl"; (described in "The Pesticide Manual", 8th ed. (1987), p. 267, Ed. C. R. Worthing; The British Crop Protection Council, Thornton Heath, GB).

It has surprisingly been found that a quantitatively variable combination of two active ingredients, on the one hand compound I and, on the other hand, an active substance from the above-mentioned compound classes II, III, IV, V, VI, VII and VIII, exhibits a synergistic action that is advantageously suitable for controlling weeds in crops of useful plants, especially in maize. These synergistic combinations are suitable for controlling the majority of important weeds, especially maize weeds, without damaging the cultivated plant.

The principal weeds in cereal crops, such as species of the monocotyledonous genera Alopecurus, Avena and Setaria, and of the dicotyledonous genera Chrysanthemum, Galium, Sinapis, Stellaria and Veronica, are destroyed selectively both in the pre-emergence and the post-emergence process.

There is therefore proposed according to the present invention a novel synergistic composition for the selective control of weeds that contains as active ingredient N-[2-(methoxycarbonyl)phenyl]sulfonyl-N'-(4,6-bis-difluoromethoxypyrimidin-2-yl)-urea of formula I

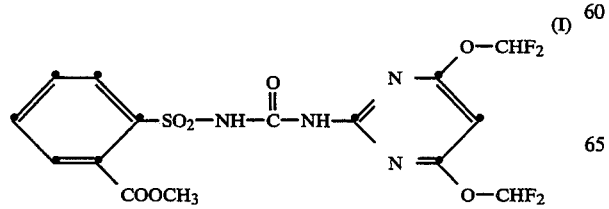

together with a synergistically effective amount of a further active ingredient a) of formula II

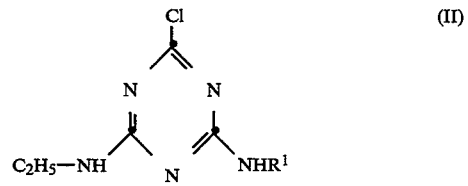

wherein
$R^1$ is isopropyl, tert.-butyl or 1-cyano-1-methylethyl, or b) of formula III

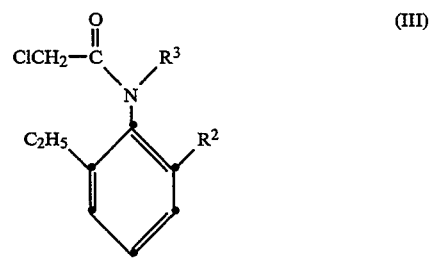

wherein
$R^2$ is methyl or ethyl and
$R^3$ is methoxymethyl or 2-methoxy-1-methylethyl, or c) of formula IV

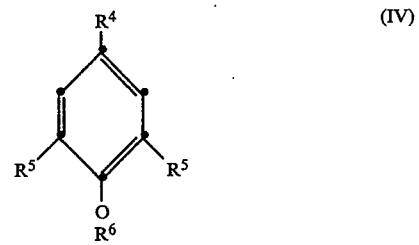

wherein
$R^5$ is bromine or iodine and
$R^4$ is CN or the radical

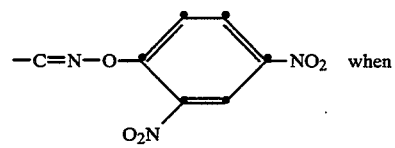 when $R^6$ is hydrogen, or
$R^4$ is CN when
$R^6$ is CO—(CH$_2$)$_6$—CH$_3$, or d) of formula V

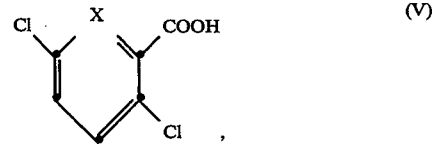

wherein

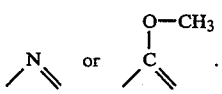

e) of formula VI

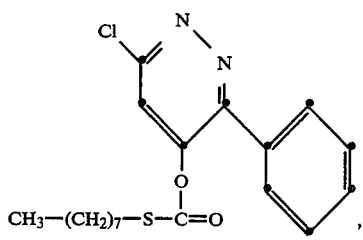

or f) of formula VII

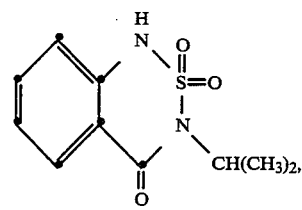

or g) of a 4-chlorophenoxyacetic acid derivative of formula VIII

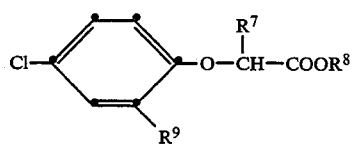

wherein
R$^7$ is hydrogen; or methyl;
R$^8$ is hydrogen; C$_1$-C$_8$alkyl; C$_1$-C$_4$alkoxy-C$_1$-C$_2$alkyl; or a cation equivalent of an alkali metal or an alkaline earth metal, or of an ammonium, di-(C$_1$-C$_4$alkylammonium, dihydroxyethylammonium or trihydroxyethylammonium ion; and
R$^9$ is chlorine; or methyl;
and, if desired, other adjuvants and/or carriers.

Attention is drawn to a composition according to the invention that contains, in addition to the compound of formula I, a synergistically effective amount of a compound of formula IIa, IIb, IIc, IIIa, IIIb, IVa, IVb, IVc, IVd, Va, Vb, VI, VII, VIIIa, VIIIb, VIIIc, VIIId, VIIIe, VIIIf, VIIIg, VIIIh, VIIIi, VIIIj, VIIIk, VIIIl or VIIIm.

The active ingredient combinations according to the invention can be used both pre-emergence and post-emergence. In addition, the seeds of the cultivated plant can be treated with a herbicidally effective amount of active ingredient combination according to the invention (seed dressing). The active ingredient combination according to the invention is thus applied when the seeds of the cultivated plants are sown.

A combination of compound I with the compounds of the formula II, IV, V, VI, VII or VIII is especially suitable for post-emergence application while a combination of compound I with compounds of formula III is preferred for pre-emergence application.

The active ingredient combinations according to the invention are especially suitable for maize.

It is extremely surprising that a combination of the compound of formula I with a compound of formula II, III, IV, V, VI, VII or VIII not only brings about an additive broadening of the spectrum of action to cover weeds that are normally associated with maize, which would be expected in principle, but also achieves a synergistic effect that broadens in two respects the range of action of the active substances that are combined with one another.

Firstly, the rates of application of the individual compounds I, II, III, IV, V, VI, VII or VIII are markedly reduced while the high level of action is maintained. Secondly, the combined mixture still achieves a high degree of weed control even in cases where the two compounds individually were entirely ineffective when used at too low a rate of application. The result of this is a considerable broadening of the weed spectrum and an additional increase in the safety margin in maize, as is necessary and desirable in case of inadvertent overdosage of the active ingredient.

The active ingredient combination according to the invention preferably contains the compounds of formula II, III, IV, V, VI, VII or VIII in the same amount as compound I or in excess relative to the amount of compound I.

The mixture ratio can be chosen as desired within wide limits. Ratios of I to II, III, IV, V, VI, VII or VIII of from 1:1 to 1:500, especially from 1:2 to 1:200, and, more especially, from 1:2 to 1:100, are preferred.

The optimum ratios of the individual compound components can be determined by biological tests.

The ratios of the individual compound components can vary in accordance with the type of weed to be controlled and in dependence on the particular form of application.

The active ingredient combinations according to the invention exhibit excellent action against weeds, without affecting the useful plant crop to any appreciable extent, at a rate of application of from 0.005 to 3.0 kg, preferably from 0.01 to 1.0 kg, of active substance per hectare.

The formulations, i.e. the compositions, preparations or mixtures containing the compound (active ingredient) mixture according to the invention and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues e.g. cork powder or sawdust.

Particularly advantageous application-promoting adjuvants which are able to reduce substantially the rate of application are also natural (animal or vegetable) or synthetic phospholipids of the series of the cephalins and lecithins, e.g. phosphatidylethanolamine, phosphatidylserine, phosphatidylcholine, sphingomyelin, phosphatidylinositol, phosphatidylglycerol, lysolecithin, plasmalogens or cardiolipin, which can be obtained e.g. from animal or vegetable cells, especially the brain, heart, lung, liver, egg yolks or soybeans. Commercial mixtures that may be used are e.g. phosphatidylcholine mixtures. Synthetic phospholipids are e.g. dioctanoylphosphatidylcholine and dipalmitoylphosphatidylcholine.

Suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyllaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$-alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, inter alia, in the following publications:

"1985 International Mc Cutcheon's Emulsifiers & Detergents", Glen Rock N.J. USA, 1985", "H. Stache, "Tensid-Taschenbuch", 2nd edition, C. Hanser Verlag, Munich, Vienna 1981, M. and J. Ash, "Encyclopedia of Surfactants", Vol. I-III, Chemical Publishing Co., New York, 1980–1981.

The agrochemical compositions usually contain 0.1 to 95%, preferably 0.1 to 80%, of the mixture of compounds of the formulae I and II, III, IV, V, VI, VII or VIII, 1 to 99.9% of a solid or liquid adjuvant, and 0 to 25%, preferably 0.1 to 25%, of a surfactant.

Preferred formulations are made up, especially, as follows: (throughout, percentages are by weight).

| Emulsifiable concentrates | | |
|---|---|---|
| active ingredient mixture: | 1 to 20%, | preferably 5 to 10% |
| surface-active agent: | 5 to 30%, | preferably 10 to 20% |
| liquid carrier: | 50 to 94%, | preferably 70 to 85% |
| Dusts | | |
| active ingredient mixture: | 0.1 to 10%, | preferably 0.1 to 1% |
| solid carrier: | 99.9 to 90%, | preferably 99.9 to 99% |
| Suspension concentrates | | |
| active ingredient mixture: | 5 to 75%, | preferably 10 to 50% |
| water: | 94 to 25%, | preferably 88 to 30% |
| surface-active agent: | 1 to 40%, | preferably 2 to 30% |
| Wettable powders | | |
| active ingredient mixture: | 0.5 to 90%, | preferably 1 to 80% |
| surface-active agent: | 0.5 to 20%, | preferably 1 to 15% |
| solid carrier: | 5.0 to 95%, | preferably 15 to 90% |
| Granulates | | |
| active ingredient mixture: | 0.5 to 30%, | preferably 3 to 15% |
| solid carrier: | 99.5 to 70%, | preferably 97 to 85% |

Whereas commercial products will preferably be formulated as concentrates, the end user will normally employ dilute formulations. The forms of application can be diluted to concentrations as low as 0.001% of active ingredient.

Other biocidal active ingredients or compositions can be mixed with the described compositions according to the invention. For example, the novel compositions may contain, in addition to the mentioned compounds of the general formula I and of the formula II, III, IV, V, VI, VII or VIII, insecticides, fungicides, bactericides, fungistatics, bacteriostatics or nematicides in order to broaden the spectrum of action.

The compositions according to the invention can generally be formulated, in detail, in accordance with the following Examples:

FORMULATION EXAMPLES

Example F1

Formulation Examples for synergistic active ingredient mixtures of the formulae I and II, III, IV, V, VI, VII or VIII (throughout, percentages are by weight)

| a) Wettable powders | a) | b) | c) | d) |
|---|---|---|---|---|
| compound I and | 10% | 20% | 5% | 30% |
| one of the compounds II, III, IV, V, VI, VII and VIII | 10% | 40% | 15% | 30% |
| sodium lignosulfonate | 5% | 5% | 5% | 5% |
| sodium lauryl sulfate | 3% | — | 3% | — |
| sodium diisobutyl-naphthalenesulfonate | — | 6% | — | 6% |
| octylphenol polyethylene glycol ether (7-8 moles of ethylene oxide) | — | 2% | — | 2% |
| highly dispersed silicic acid | 5% | 27% | 5% | 27% |
| kaolin | 67% | — | 67% | — |

The active ingredient mixture is thoroughly mixed with toe adjuvants and the mixture is thoroughly ground in a suitable mill, affording wettable powders which can be diluted with water to give suspensions of the desired concentration.

| b) Emulsifiable concentrate | a) | b) | c) |
|---|---|---|---|
| compound I and | 5% | 5% | 12% |
| one of the compounds II, III, IV, V, VI, VII and VIII | 5% | 20% | 13% |
| octylphenol polyethylene glycol ether (4-5 moles of ethylene oxide) | 3% | 3% | 3% |
| calcium dodecylbenzenesulfonate | 3% | 3% | 2% |
| castor oil polyglycol ether (36 moles of ethylene oxide) | 4% | 4% | 4% |
| cyclohexanone | 30% | 30% | 31% |
| xylene mixture | 50% | 35% | 35% |

Emulsions of any required concentration can be obtained from this concentrate by dilution with water.

| c) Dusts | a) | b) | c) | d) |
|---|---|---|---|---|
| compound I and | 2% | 4% | 2% | 4% |
| one of the compounds II, III, IV, V, VI, VII and VIII | 3% | 4% | 4% | 8% |
| talcum | 95% | — | 94% | — |
| kaolin | — | 92% | — | 88% |

Ready-for-use dusts are obtained by mixing the active ingredient mixture with the carrier and grinding the mixture in a suitable mill.

| d) Extruder granulate | a) | b) | c) |
|---|---|---|---|
| compound I and | 5% | 3% | 5% |
| one of the compounds II, III, IV, V, VI, VII and VIII | 5% | 7% | 15% |
| sodium lignosulfonate | 2% | 2% | 2% |
| carboxymethylcellulose | 1% | 1% | 1% |
| kaolin | 87% | 87% | 77% |

The active ingredient mixture is mixed and ground with the adjuvants, and the mixture is subsequently moistened with water. The mixture is extruded and then dried in a stream of air.

| e) Coated granulate | a) | b) |
|---|---|---|
| compound I and | 1.5% | 3% |
| one of the compounds II, III, IV, V, VI, VII and VIII | 1.5% | 5% |
| polyethylene glycol (mol. wt. 200) | 3% | 3% |
| kaolin | 94% | 89% |

The finely ground active ingredient mixture is uniformly applied, in a mixer, to the kaolin moistened with polyethylene glycol. Non-dusty coated granulates are obtained in this manner.

| f) Suspension concentrate | a) | b) |
|---|---|---|
| compound I and | 20% | 20% |
| one of the compounds II, III, IV, V, VI, VII and VIII | 20% | 40% |
| ethylene glycol | 10% | 10% |
| nonylphenol polyethylene glycol ether (15 moles of ethylene oxide) | 6% | 6% |
| sodium lignosulfonate | 10% | 10% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 12% |

The finely ground active ingredient mixture is intimately mixed with the adjuvants, giving a suspension concentrate from which suspensions of any desired concentration can be obtained by dilution with water.

A synergistic effect is always present in the case of herbicides when the herbicidal action of the combination of compounds I and II, III, IV, V, VI, VII or VIII is greater than the total action of the active ingredients applied individually.

The expected herbicidal action Ae for a given combination of two herbicides can be calculated as follows (cf. COLBY, S. R., "Calculating synergistic and antagonistic response of herbicide combinations", Weeds 15, pages 20–22, 1967):

$$Ae = X + \frac{Y \cdot (100 - X)}{100}$$

in which:
X = percentage inhibition of growth in the case of treatment with a herbicide I at a rate of application of p kg per hectare in comparison with the untreated control (=0%)
Y = percentage inhibition of growth in the case of treatment with a herbicide II, III, IV, V, VI, VII or VIII at a rate of application of q kg per hectare in comparison with the untreated control Ae = expected herbicidal action (percentage inhibition of growth in comparison with the untreated control) after treatment with herbicide mixture I and II, III, IV, V, VI, VII or VIII at a rate of application of p+q kg active ingredient per hectare.

If the action actually observed is greater than the expected value Ae then synergism has been achieved.

The synergistic effect of the combinations of compounds I and II, III, IV, V, VI, VII or VIII is demonstrated in the following Examples.

BIOLOGICAL EXAMPLES

Example B1: Pre-Emergence Test

In a greenhouse, the seeds of the test plants are sown in plastic pots containing 0.5 l of sterilised soil. One day after sowing, the surface of the soil is sprayed with an aqueous dispersion of the active ingredient combination.

The rate of application of the active substance is adjusted by suitable dilution of the concentrate. 50 ml of dispersion are sprayed per m². The test plants are further cultivated in the greenhouse and are watered daily. An evaluation is made 20 days after sowing and application. The percentage inhibition of growth is recorded in comparison with the untreated control plants. The following linear scale was used as a rating:

100% = plants withered
50% = medium effect
0% = as untreated control plants

The results of the test are shown together with the expected values, calculated in accordance with the above-mentioned Colby formula, in Tables a) and b). The Tables indicate the rates of application of the active ingredients and also the tested cultivated plants and weeds.

In Tables a) and b), the expected values for the test plant, calculated according to Colby, are shown in column Ae in comparison with the values in column A which were ascertained experimentally.

a) pre-emergence activity of mixtures of I and IIIa

Evaluation: 20 days after application in comparison with the untreated control plants

| active ingredient [g/ha] | | test plant action [%] | | | |
|---|---|---|---|---|---|
| | | maize LG9 | | Abutilon theophr. | |
| I | IIIa | Ae | A | Ae | A |
| 10 | — | — | 0 | — | 20 |
| — | 30 | — | 0 | — | 0 |
| — | 60 | — | 0 | — | 0 |
| — | 120 | — | 0 | — | 0 |
| — | 250 | — | 0 | — | 0 |
| 10 | 30 | 0 | 0 | 20 | 60 |
| 10 | 60 | 0 | 0 | 20 | 60 |
| 10 | 120 | 0 | 0 | 20 | 50 |
| 10 | 250 | 0 | 0 | 20 | 50 |

Ae = expected value calculated according to Colby
A = action ascertained experimentally b) pre-emergence activity of mixtures of I and IIIb Evaluation: 20 days after application in comparison with untreated control plants

| active ingredient [g/ha] | | test plant action [%] | | | |
|---|---|---|---|---|---|
| | | maize LG9 | | Abutilon theophr. | |
| I | IIIb | Ae | A | Ae | A |
| 10 | — | — | 0 | — | 20 |
| — | 30 | — | 0 | — | 0 |
| — | 60 | — | 0 | — | 0 |
| — | 120 | — | 0 | — | 0 |
| — | 250 | — | 0 | — | 0 |
| — | 500 | — | 5 | — | 10 |
| 10 | 30 | 0 | 0 | 20 | 30 |
| 10 | 60 | 0 | 0 | 20 | 40 |
| 10 | 120 | 0 | 0 | 20 | 40 |
| 10 | 250 | 0 | 0 | 24 | 40 |
| 10 | 500 | 5 | 0 | 24 | 70 |

Ae = expected value calculated according to Colby
A = action determined experimentally

Example B2: Post-Emergence Test

The test plants are grown in plastic pots containing 0.5 l of sterilised soil. After emergence, the plants are sprayed in the 2–3 leaf stage (about 2 weeks after sowing) with an aqueous dispersion of the active ingredient combinations. The amount of spray liquor is 50 ml per m². The rate of application of active substances is adjusted by suitable dilution of the concentrate. The test plants are further cultivated in the greenhouse and are watered daily. An evaluation is made 20 days after application. The degree of damage to the plants is evaluated as a percentage in accordance with the same rating as was used in the pre-emergence test.

The results of the test are shown together with the expected values, calculated in accordance with the above-mentioned Colby formula, in the following Tables a, b, c, d and e. Each table indicates the rates of application of the active ingredients and also the tested cultivated plants and weeds.

Here too, the expected values calculated according to Colby are given in column Ae and are compared with the values in column A which were ascertained experimentally.

a) post-emergence activity of mixtures of I and IIa

Evaluation: 20 days after application in comparison with the untreated control plants

| active ingredient [g/ha] | | test plant action [%] | | | | | | | |
|---|---|---|---|---|---|---|---|---|---|
| | | maize LG9 | | Abutilon theophr. | | Sorghum halep. | | Chenopodium album. | |
| I | IIa | Ae | A | Ae | A | Ae | A | Ae | A |
| 10 | — | — | 0 | — | 60 | — | 85 | — | 30 |
| — | 30 | — | 0 | — | 0 | — | 0 | — | 0 |
| — | 60 | — | 0 | — | 0 | — | 0 | — | 0 |
| — | 120 | — | 0 | — | 0 | — | 0 | — | 0 |
| — | 250 | — | 0 | — | 0 | — | 0 | — | 0 |
| — | 500 | — | 0 | — | 10 | — | 0 | — | 0 |
| 10 | 30 | 0 | 0 | 60 | 70 | 85 | 85 | 30 | 70 |
| 10 | 60 | 0 | 0 | 60 | 70 | 85 | 85 | 30 | 70 |
| 10 | 120 | 0 | 0 | 60 | 80 | 85 | 90 | 30 | 70 |
| 10 | 250 | 0 | 0 | 60 | 80 | 85 | 90 | 30 | 70 |
| 10 | 500 | 0 | 0 | 64 | 99 | 85 | 90 | 30 | 70 |

Ae = expected value calculated according to Colby
A = action ascertained experimentally b) post-emergence activity of mixtures of I and IIb Evaluation: 20 days after application in comparison with the untreated control plants

| active ingredient [g/ha] | | test plant action [%] | | | | | |
|---|---|---|---|---|---|---|---|
| | | maize LG9 | | Ipomoea purpurea | | Chenopodium album. | |
| I | IIb | Ae | A | Ae | A | Ae | A |
| 10 | — | — | 0 | — | 20 | — | 30 |
| — | 80 | — | 0 | — | 0 | — | 0 |
| — | 150 | — | 0 | — | 10 | — | 0 |
| — | 300 | — | 0 | — | 70 | — | 0 |
| — | 600 | — | 10 | — | 90 | — | 10 |
| 10 | 80 | 0 | 0 | 20 | 20 | 30 | 40 |
| 10 | 150 | 0 | 0 | 28 | 20 | 30 | 40 |
| 10 | 300 | 0 | 0 | 76 | 100 | 30 | 50 |
| 10 | 600 | 0 | 0 | 79 | 100 | 37 | 50 |

Ae = expected value calculated according to Colby
A = action ascertained experimentally c) post-emergence activity of mixtures of I and IIc
Evaluation: 20 days after application in comparison with the untreated control plants

| active ingredient [g/ha] | | test plant avtion [%] | | | |
|---|---|---|---|---|---|
| | | maizr LG9 | | Chenopodium album. | |
| I | IIc | Ae | A | Ae | A |
| 10 | — | — | 0 | — | 30 |
| — | 60 | — | 0 | — | 0 |
| — | 125 | — | 0 | — | 0 |
| — | 250 | — | 0 | — | 0 |
| — | 500 | — | 0 | — | 0 |
| — | 1000 | — | 0 | — | 0 |
| 10 | 60 | 0 | 0 | 30 | 70 |
| 10 | 125 | 0 | 0 | 30 | 70 |
| 10 | 250 | 0 | 0 | 30 | 70 |
| 10 | 500 | 0 | 0 | 30 | 70 |
| 10 | 1000 | 0 | 0 | 30 | 80 |

Ae = expected value calculated according to Colby
A = action ascertained experimentally d) post-emergence activity of mixtures of I and IVa
Evaluation: 20 days after application in comparison with the untreated control plants

| active ingredient [g/ha] | | test plant action [%] | | | | | | | |
|---|---|---|---|---|---|---|---|---|---|
| | | maize LG9 | | Amaranth. retrofl. | | Chenopodium album. | | Ipomea purpurea | |
| I | IVa | Ae | A | Ae | A | Ae | A | Ae | A |
| 10 | — | — | 10 | — | 50 | — | 30 | — | 10 |
| — | 60 | — | 0 | — | 10 | — | 10 | — | 0 |
| — | 125 | — | 0 | — | 40 | — | 20 | — | 0 |
| — | 250 | — | 0 | — | 50 | — | 20 | — | 10 |
| — | 500 | — | 0 | — | 70 | — | 40 | — | 10 |
| — | 1000 | — | 0 | — | 90 | — | 98 | — | 50 |
| 10 | 60 | 10 | 0 | 55 | 80 | 37 | 40 | 10 | 10 |
| 10 | 125 | 10 | 0 | 70 | 97 | 44 | 60 | 10 | 30 |
| 10 | 250 | 10 | 0 | 75 | 97 | 44 | 80 | 19 | 30 |
| 10 | 500 | 10 | 10 | 85 | 95 | 58 | 95 | 19 | 70 |
| 10 | 1000 | 10 | 10 | 95 | 98 | 99 | 100 | 55 | 80 |

Ae = expected value calculated according to Colby
A = action ascertained experimentally e) post-emergence activity of mixtures of I and IVd
Evaluation: 20 days after application in comparison with the untreated control plants

| active ingredient [g/ha] | | test plant action [%] | | | | | | | |
|---|---|---|---|---|---|---|---|---|---|
| | | maize LG9 | | Sorghum halep. | | Chenopodium album. | | Ipomea purpurea | |
| I | IVa | Ae | A | Ae | A | Ae | A | Ae | A |
| 10 | — | — | 0 | — | 50 | — | 30 | — | 20 |
| 20 | — | — | 10 | — | 80 | — | 70 | — | 30 |
| — | 40 | — | 0 | — | 0 | — | 0 | — | 10 |
| — | 80 | — | 0 | — | 0 | — | 40 | — | 20 |
| — | 150 | — | 10 | — | 0 | — | 80 | — | 20 |
| — | 300 | — | 10 | — | 10 | — | 90 | — | 30 |
| — | 600 | — | 20 | — | 10 | — | 99 | — | 50 |
| 10 | 40 | 0 | 0 | 50 | 50 | 30 | 50 | 28 | 40 |
| 10 | 80 | 0 | 0 | 50 | 60 | 58 | 60 | 36 | 40 |
| 10 | 150 | 10 | 0 | 50 | 80 | 86 | 95 | 36 | 80 |
| 10 | 300 | 10 | 0 | 55 | 80 | 93 | 99 | 44 | 80 |
| 10 | 600 | 20 | 10 | 55 | 95 | 99 | 99 | 60 | 80 |
| 20 | 40 | 10 | 0 | 80 | 80 | 70 | 95 | 37 | 40 |
| 20 | 80 | 10 | 0 | 80 | 90 | 82 | 90 | 44 | 50 |
| 20 | 150 | 19 | 0 | 80 | 95 | 94 | 95 | 44 | 50 |
| 20 | 300 | 19 | 10 | 82 | 98 | 97 | 100 | 51 | 80 |
| 20 | 600 | 28 | 15 | 82 | 100 | 100 | 100 | 65 | 95 |

Ae = expected value calculated according to Colby
A = action ascertained experimentally

We claim:

1. A herbicidal composition consisting essentially of a herbicidally effective amount of a mixture of 1 part by weight of N-[(2-methoxycarbonyl)phenyl]-sulfonyl-N'-(4,6-bis-difluoromethoxypyrimidin-2-yl)-urea of the formula I $$\text{(I)}$$

together with 2 to 100 parts by weight of the acetanilide of the formula III $$\text{(III)}$$

and an agriculturally acceptable carrier.

2. A composition according to claim 1, which consists essentially of, per 1 part by weight of the compound of the formula I, 2 to 25 parts by weight of the compound of formula III.

3. A method for the selective control of weeds in crops of useful plants, consisting essentially of applying to the crop area a selectively herbicidally effective amount of a composition according to claim 1.

4. A method according to claim 3 for the selective pre- or post-emergence control of weeds in maize crops.

5. A method according to claim 3, wherein the compound of formula III is present in a ratio of 2 to 25 parts by weight per 1 part by weight of the compound of the formula I.

* * * * *